(12) United States Patent
Bar-El et al.

(10) Patent No.: US 9,795,534 B2
(45) Date of Patent: Oct. 24, 2017

(54) COMPLIANT COUPLING ASSEMBLY FOR CARTRIDGE COUPLING OF A DRUG DELIVERY DEVICE

(71) Applicant: MEDIMOP Medical Projects Ltd., Ra'anana (IL)

(72) Inventors: Yossi Bar-El, Beit Arye (IL); Evgeni Venislavski, Rosh Ha Ain (IL); Tomer Solomon, Modiin (IL); Reuven Y. Filman, Netanya (IL)

(73) Assignee: MEDIMOP MEDICAL PROJECTS LTD., Ra'anana (IL)

(*) Notice: Subject to any disclaimer, the term of this patent is extended or adjusted under 35 U.S.C. 154(b) by 321 days.

(21) Appl. No.: 14/638,696

(22) Filed: Mar. 4, 2015

(65) Prior Publication Data

US 2016/0256352 A1  Sep. 8, 2016

(51) Int. Cl.

| | |
|---|---|
| *A61J 1/14* | (2006.01) |
| *A61M 5/178* | (2006.01) |
| *A61M 5/145* | (2006.01) |
| *A61M 5/14* | (2006.01) |
| *A61M 5/162* | (2006.01) |
| *A61M 5/34* | (2006.01) |

(52) U.S. Cl.
CPC .......... *A61J 1/1406* (2013.01); *A61M 5/1413* (2013.01); *A61M 5/1456* (2013.01); *A61M 5/162* (2013.01); *A61M 5/1782* (2013.01); *A61M 2005/341* (2013.01); *A61M 2209/045* (2013.01)

(58) Field of Classification Search
CPC .......... A61M 5/1456; A61M 2005/341; A61M 39/10; A61M 5/1782; A61M 2209/145; A61M 5/1413; A61M 5/162; A61J 1/1406
See application file for complete search history.

(56) References Cited

U.S. PATENT DOCUMENTS

| | | |
|---|---|---|
| 3,994,295 A | 11/1976 | Wulff |
| 4,601,702 A | 7/1986 | Hudson |

(Continued)

FOREIGN PATENT DOCUMENTS

| | | |
|---|---|---|
| EP | 0401179 A1 | 12/1990 |
| EP | 1249250 A1 | 10/2002 |

(Continued)

OTHER PUBLICATIONS

Extended Search Report dated Jun. 13, 2016 in EP Application No. 16157430.6.

(Continued)

*Primary Examiner* — Leslie Deak
(74) *Attorney, Agent, or Firm* — Panitch Schwarze Belisario & Nadel LLP

(57) ABSTRACT

An assembly for coupling a drug delivery device to a cartridge is disclosed. Optionally the assembly includes a coupling, for example a cannula, having one end extending toward the cartridge. The cartridge is optionally aligned by a guide. Optionally the cartridge has a limited freedom of movement. The coupling is optionally supported by a mount. In some embodiments, the mount is compliant enough that the end of the coupling that extends toward may move to said limited freedom of movement under a force less than a leak threshold of the connection between the coupler and the cartridge.

13 Claims, 10 Drawing Sheets

(56) References Cited

U.S. PATENT DOCUMENTS

| | | |
|---|---|---|
| 4,886,499 A | 12/1989 | Cirelli et al. |
| 4,919,596 A | 4/1990 | Slate et al. |
| 4,950,246 A | 8/1990 | Muller |
| 5,097,122 A | 3/1992 | Colman et al. |
| 5,109,850 A | 5/1992 | Blanco et al. |
| 5,131,816 A | 7/1992 | Brown et al. |
| 5,211,638 A | 5/1993 | Dudar et al. |
| 5,254,096 A | 10/1993 | Rondelet et al. |
| 5,383,865 A | 1/1995 | Michel |
| 5,501,665 A | 3/1996 | Jhuboo et al. |
| 5,593,390 A | 1/1997 | Castellano et al. |
| 5,616,132 A | 4/1997 | Newman |
| 5,643,218 A | 7/1997 | Lynn et al. |
| 5,647,853 A | 7/1997 | Feldmann et al. |
| 5,690,618 A | 11/1997 | Smith et al. |
| D393,314 S | 4/1998 | Meisner et al. |
| 5,800,420 A | 9/1998 | Gross et al. |
| 5,807,375 A | 9/1998 | Gross et al. |
| 5,814,020 A | 9/1998 | Gross |
| 5,851,197 A | 12/1998 | Marano et al. |
| 5,858,001 A | 1/1999 | Tsals et al. |
| 5,858,008 A | 1/1999 | Capaccio |
| 5,931,814 A | 8/1999 | Alex et al. |
| 5,957,895 A | 9/1999 | Sage et al. |
| 5,993,423 A | 11/1999 | Choi |
| 6,004,297 A | 12/1999 | Steenfeldt-Jensen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,362,591 B1 | 3/2002 | Moberg |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,517,517 B1 | 2/2003 | Farrugia et al. |
| D471,274 S | 3/2003 | Diaz et al. |
| D471,983 S | 3/2003 | Hippolyte et al. |
| 6,555,986 B2 | 4/2003 | Moberg |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 * | 11/2003 | Lavi ............... A61J 1/2089 604/182 |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,699,218 B2 | 3/2004 | Flaherty et al. |
| 6,749,587 B2 | 6/2004 | Flaherty |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,817,990 B2 | 11/2004 | Yap et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 7,001,360 B2 | 2/2006 | Veasey et al. |
| 7,048,715 B2 | 5/2006 | Diaz et al. |
| 7,060,059 B2 | 6/2006 | Keith et al. |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,247,149 B2 | 7/2007 | Beyerlein |
| 7,247,150 B2 | 7/2007 | Bierman |
| 7,250,037 B2 | 7/2007 | Shermer et al. |
| 7,267,669 B2 | 9/2007 | Staunton et al. |
| 7,303,549 B2 | 12/2007 | Flaherty et al. |
| 7,384,413 B2 | 6/2008 | Gross et al. |
| 7,390,314 B2 | 6/2008 | Stutz, Jr. et al. |
| 7,407,493 B2 | 8/2008 | Cane' |
| 7,455,663 B2 | 11/2008 | Bikovsky |
| 7,465,290 B2 | 12/2008 | Reilly |
| 7,497,842 B2 | 3/2009 | Diaz et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,297 B2 | 6/2011 | Radmer et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 7,998,116 B2 | 8/2011 | Mernoe |
| 7,998,117 B2 | 8/2011 | Gross et al. |
| 8,002,752 B2 | 8/2011 | Yodfat et al. |
| 8,021,357 B2 | 9/2011 | Tanaka et al. |

(56) References Cited

U.S. PATENT DOCUMENTS

| | | |
|---|---|---|
| 8,025,658 B2 | 9/2011 | Chong et al. |
| 8,029,459 B2 | 10/2011 | Rush et al. |
| 8,029,460 B2 | 10/2011 | Rush et al. |
| 8,029,469 B2 | 10/2011 | Ethelfeld |
| 8,034,019 B2 | 10/2011 | Nair et al. |
| 8,038,648 B2 | 10/2011 | Marksteiner |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,062,259 B2 | 11/2011 | Nycz et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,296 B2 | 6/2012 | Jennewine |
| 8,206,351 B2 | 6/2012 | Sugimoto et al. |
| 8,221,356 B2 | 7/2012 | Enggaard et al. |
| 8,221,359 B2 | 7/2012 | Kristensen et al. |
| 8,226,607 B2 | 7/2012 | Carter et al. |
| 8,226,608 B2 | 7/2012 | Mernoe |
| 8,234,769 B2 | 8/2012 | Leidig |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,361,028 B2 | 1/2013 | Gross et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,715,237 B2 | 5/2014 | Moberg et al. |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,808,269 B2 | 8/2014 | Bazargan et al. |
| 8,810,394 B2 | 8/2014 | Kalpin |
| 8,864,739 B2 | 10/2014 | Moberg et al. |
| 8,870,818 B2 | 10/2014 | Alderete, Jr. et al. |
| 8,992,475 B2 | 3/2015 | Mann et al. |
| 9,011,371 B2 | 4/2015 | Moberg et al. |
| 9,033,924 B2 | 5/2015 | Yavorsky |
| 9,050,406 B2 | 6/2015 | Kow et al. |
| 2001/0034502 A1 | 10/2001 | Moberg et al. |
| 2002/0040208 A1 | 4/2002 | Flaherty et al. |
| 2002/0055711 A1 | 5/2002 | Lavi et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0085215 A1 | 5/2004 | Moberg et al. |
| 2004/0260233 A1 | 12/2004 | Garibotto et al. |
| 2005/0065472 A1 | 3/2005 | Cindrich et al. |
| 2005/0071487 A1 | 3/2005 | Lu et al. |
| 2005/0171487 A1 | 8/2005 | Haury et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0238507 A1 | 10/2005 | Dilanni et al. |
| 2006/0095014 A1 | 5/2006 | Ethelfeld |
| 2006/0122577 A1 | 6/2006 | Poulsen et al. |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0191770 A1 | 8/2007 | Moberg et al. |
| 2007/0282269 A1 | 12/2007 | Carter et al. |
| 2008/0033369 A1 | 2/2008 | Kohlbrenner et al. |
| 2008/0051711 A1 | 2/2008 | Mounce et al. |
| 2008/0059133 A1 | 3/2008 | Edwards et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0275425 A1 | 11/2008 | Strickler et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |

(56) References Cited

U.S. PATENT DOCUMENTS

| | | |
|---|---|---|
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0198157 A1 | 8/2010 | Gyrn et al. |
| 2010/0204657 A1 | 8/2010 | Yodfat et al. |
| 2010/0212407 A1 | 8/2010 | Stringham et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1* | 3/2011 | Cabiri ............... A61M 5/14248 604/411 |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0201998 A1 | 8/2011 | Pongpairochana et al. |
| 2011/0224614 A1 | 9/2011 | Moberg et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0078217 A1 | 3/2012 | Smith et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0310153 A1 | 12/2012 | Moberg et al. |
| 2013/0012873 A1 | 1/2013 | Gross et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0148270 A1 | 6/2013 | Fujioka et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253472 A1 | 9/2013 | Cabiri |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1* | 3/2014 | Moia .................... A61M 39/10 137/15.01 |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| EP | 2412395 A1 | 2/2012 |
| EP | 2712650 A1 | 4/2014 |
| WO | 9009202 A1 | 8/1990 |
| WO | 9632975 A1 | 10/1996 |
| WO | 2011090955 A1 | 7/2011 |
| WO | 2011141907 A1 | 11/2011 |

OTHER PUBLICATIONS

Edwin Chan, Yuh-Fun Maa, Ph.D and David Overcashier; Manufacturing Consideration in Developing a Prefilled Syringe—Investigating the Effect of Headspace Pressure; American Pharmaceutical Review, May 8, 2012 and Appendix 3 Measurement of Leakage of Tuberculin Syringes; World Health Organization Monograph Series No. 12; BCG Vaccination, editors Lydia Edwards, Carroll Palmer and Knut Magnus; Tuberculosis Research Office World Health Organization Copenhagen; World Health Organization; Palais Des Nations, Geneva, 1953.

* cited by examiner

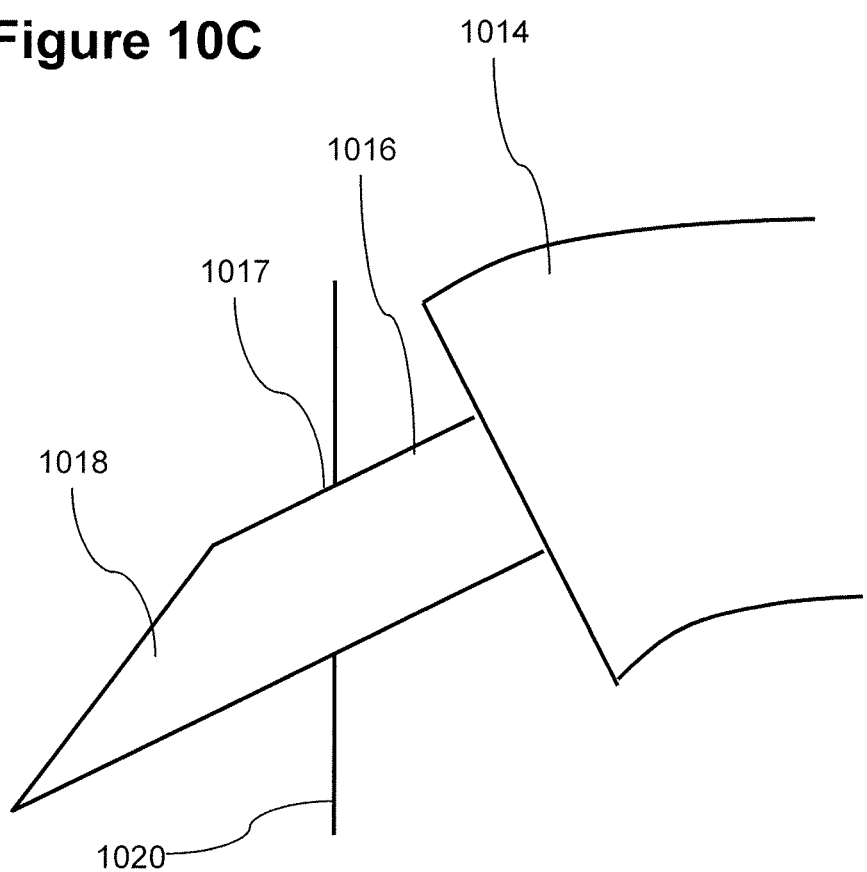

COMPLIANT COUPLING ASSEMBLY FOR CARTRIDGE COUPLING OF A DRUG DELIVERY DEVICE

CROSS REFERENCE TO RELATED APPLICATION

This application is related to U.S. patent application titled "FLEXIBLY MOUNTED CARTRIDGE ALIGNMENT COLLAR FOR DRUG DELIVERY DEVICE" to the same Applicant and filed on the same day, which is hereby incorporated by reference in its entirety.

BACKGROUND OF THE INVENTION

The present invention, in some embodiments thereof, relates to a coupling system for a drug cartridge, more particularly, but not exclusively, to a coupling system including a cannula to be inserted through a septum.

U.S. Patent Application Publication No. 20110054400 discloses that, "a piercing member for piercing a membrane may be arranged within a housing and supported by a compliant that may be for allowing articulation of the piercing member relative to the housing in a case where the piercing member is in the membrane and moved relative to the housing."

U.S. Pat. No. 6,595,960 discloses, "An apparatus and method of providing a flexible needle assembly for use with a medication delivery pen. The flexible needle assembly includes a needle cannula having proximal and distal points and a hub coupled to the needle cannula. The hub includes a flexible roof, or ball-and-socket arrangement, that permits the needle cannula to move about the centerline of the hub. The flexible roof can include one or more concentric ribs to enhance flexibility of the needle cannula about the centerline of the hub."

U.S. Pat. No. 3,994,295 discloses that, "An adapter device for mounting a hypodermic needle on a syringe barrel consists of two telescoped elements the outer of which is a casing or shell and the inner or which is a resilient tube bonded at opposite ends to a stem adapted for connection to the barrel and a needle mounting member seated over the end of the shell."

U.S. Patent Application Publication No. 20140083517 discloses "an alignment device for coupling a liquid drug cartridge with a longitudinal cartridge axis and a constricted neck portion with a cap and a pierceable septum distal from the neck portion with an adapter . . . " "The septum is perpendicular to the cartridge axis. The device comprises an adapter cannula with a longitudinal cannula axis to pierce the septum and a proximal cartridge engagement structure for axial aligned engagement with a distal end section of cartridge body. The device further comprises a distal adapter engagement structure for axial aligned engagement with the adapter. A coupling of the cartridge with the adapter is enabled via the alignment device. The adapter and the cartridge are, during the coupling, aligned by the cartridge engagement structure and the adapter engagement structure, respectively relative to each other such that the longitudinal cartridge axis and the longitudinal cannula axis form a common longitudinal axis."

U.S. Patent Application Publication No. 20120029431 discloses "A reservoir and straight-line, push-on connector assembly" . . . "for connecting the reservoir and one of a standard Luer line set and a custom Luer line set to any number of infusion pump configurations using a simple straight-line, push-on motion, wherein the push-on connector assembly is provided and configured to secure the line set and reservoir with the infusion pump. One simple straight-line, push-on motion, preferably performed by gripping an expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for connection, pump engagement, or pump function, and any pulling of the tube set will not release the reservoir as the expansion sleeve through which the tube set is routed is not moved from the securing position by tension on the tube set or Luer fitting."

U.S. Patent Application Publication No. 2013/096509 discloses "A system for a drug delivery device comprising a reservoir holder configured to hold a reservoir, and an alignment interface comprising a main body configured to be coupled to the reservoir. A first alignment feature is provided on the main body. The first alignment feature cooperates with a corresponding alignment feature provided by the reservoir holder such that when the reservoir is inserted into the holder, the first alignment feature cooperates with the corresponding alignment feature provided by the holder so as to rotate the alignment interface and thereby align the alignment interface within the holder. Thus, the reservoir may be aligned within the reservoir holder. The first alignment feature may comprise at least one protrusion provided on the main body of the interface. The system further comprises one or more coding features."

U.S. Patent Application Publication No. 2013148270 discloses a method and apparatus, "for delivery of a drug to a recipient. In some embodiments, the delivery apparatus may unseal a drug containing reservoir. In some embodiments, the delivery rate may be controlled and/or adjustable. Optionally the apparatus may be disposable. Optionally, the apparatus may have a low profile and/or be wearable and/or attachable to the recipient. Optionally, discharge of the drug and/or unsealing of the reservoir may be driven by a plunger moving parallel to the base of the apparatus. Optionally, the apparatus may release a hypodermic needle into the recipient. Optionally, release of the hypodermic needle may be in a direction non-parallel and/or orthogonal to the direction of movement of the plunger. Optionally, prior to release, the hypodermic needle may be preserved in an aseptic state by a needle opening septum sealing a needle opening. Optionally, upon release, the hypodermic needle may pierce the needle opening septum."

Additional background art includes Edwin Chan, Yuh-Fun Maa, Ph.D and David Overcashier; Manufacturing Consideration in Developing a Prefilled Syringe—Investigating the Effect of Headspace Pressure; American Pharmaceutical Review, May 8, 2012 and Appendix 3 Measurement of Leakage of Tuberculin Syringes; World Health Organization Monograph Series No. 12; BCG Vaccination, editors Lydia Edwards, Carroll Palmer and Knut Magnus; Tuberculosis Research Office World Health Organization Copenhagen; World Health Organization; Palais Des Nations, Geneva, 1953.

BRIEF SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided an assembly for coupling a drug delivery device to a cartridge sealed by a septum having a leak threshold force, the apparatus comprising: a cannula having a tip region configured to penetrate the septum, the tip region having a width; a frame including: a guide sized and shaped to secure the cartridge to the frame and a mount attached to the cannula; the mount positioned on the frame so that the tip region of the cannula protrudes through the septum of the cartridge when the cartridge is secured to the frame by the guide; the mount is compliant enough so that a force of less than a leak threshold force of the septum moves the tip region of the cannula transaxially at least distance equal to the width.

According to some embodiments of the invention, the mount is compliant enough so that a force of less than a leak threshold force of the septum moves the tip region of the cannula transaxially at least distance equal to a position deviation tolerance of the septum.

According to some embodiments of the invention, the distance is greater than a movement caused by a flexibility of the frame and the cannula under the leak threshold force.

According to some embodiments of the invention, the mount compensates for a movement of the cannula at a stress level less than a stress then a bending stress of the cannula.

According to some embodiments of the invention, the leak threshold force is 6 N.

According to some embodiments of the invention, the assembly further comprises: a base located on a side of the cannula opposite the tip region, the base inhibiting backwards movement of the tip region.

According to some embodiments of the invention, the base is positioned off axis of the cannula.

According to some embodiments of the invention, the mount is configured to bias movement of the cannula is a particular direction.

According to some embodiments of the invention, the particular direction is parallel to a face of a bevel of a tip of the cannula.

According to some embodiments of the invention, the cannula is bent at an angle ranging between 30 to 80 degrees.

According to some embodiments of the invention, the assembly further comprises: a second end of the cannula connected to a flexible fluid path.

According to some embodiments of the invention, the assembly further includes the cartridge is coupleable to the cannula by a linear movement of the cartridge with respect to the guide.

According to some embodiments of the invention, the compliant mount is flexible.

According to an aspect of some embodiments of the invention, there is provided a method of supplying a drug to a delivery device comprising: loading a cartridge containing the drug into the delivery device piercing a septum with a cannula; opening a flow path between the cannula and an internal fluid path of the drug delivery device; limiting transaxial movement of the septum to less than a first deviation tolerance; and allow transverse movement of a septum interface region of the cannula to adjust to the movement.

According to some embodiments of the invention, the transaxial movements of the cannula are caused by a stress less than a leak threshold of the septum.

According to some embodiments of the invention, the allowing movement is in one direction more than another direction.

According to some embodiments of the invention, the more movement is allowed in the direction opposite a face of a bevel of the cannula than in a direction of the face of a bevel of the cannula.

According to some embodiments of the invention, the more movement is allowed parallel to a direction faced by a bevel of the cannula than in a direction perpendicular thereto.

According to some embodiments of the invention, the allowing movement is less when there is an axial stress against a tip of the cannula than when the cannula not under axial stress.

According to some embodiments of the invention, the method where the allowing movement is elastic.

BRIEF DESCRIPTION THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

In this regard, the description taken with the drawings makes apparent to those skilled in the art how embodiments of the invention may be practiced.

In the drawings:

FIGS. 10A-10C are schematic illustrations of a system for connecting a cartridge to a drug delivery device in accordance with an embodiment of the current invention.

DESCRIPTION OF THE INVENTION

Figure 1A:
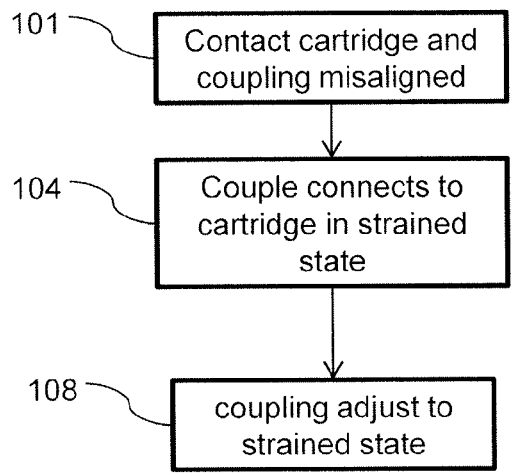
FIGS. 1A-1B are flow chart illustrations of a method of connecting a cartridge to a fluid path of a drug delivery device in accordance with an embodiment of the current invention.

The present invention, in some embodiments thereof, relates to a coupling system for a drug cartridge, more particularly, but not exclusively, to a coupling system including a cannula to be inserted through a septum.

An aspect of some embodiments of the present invention relates reducing stress on a coupling caused for example by movement of the coupled parts. For example, the coupling may include a cannula puncturing a septum of a cartridge of a drug delivery device. For example a compliant assembly may reduce stress between a cannula and a septum caused by movements of the cartridge. Misfitting and/or relative movement between a drug cartridge and the delivery device may cause relative movement between the cartridge and the coupling. Optionally, when the septum moves, the compliant assembly may permit compensating movement of a septum interface portion of the cannula reducing stress at the interface. In some embodiments, a compliant coupling assembly may allow directionally dependent displacement of the coupling. For example, the tip of the cannula may move transaxially in response to lateral movement of the septum.

In some embodiments, a frame may interconnect, orient and/or position a guide in relation to a compliant coupling assembly. For example, the frame may include a housing of a drug delivery device and/or the guide may include a guide channel in the housing. Optionally, the cartridge includes a septum near a distal end thereof. For example, the septum may be oriented perpendicular to a longitudinal axis of the cartridge (for example the axis may extend from the distal end to the proximal end of the cartridge). The coupling optionally includes cannula, for example a hollow needle oriented longitudinally near the distal end of the guide channel. In some embodiments, the cartridge may be inserted into the channel and/or the cannula (for example a beveled proximal end thereof). The proximal end of the cannula may protrude into the access channel of the cartridge and/or puncture the septum of the cartridge. After puncturing the septum, the hollow of the needle may form a flow path from the inside of the cartridge into an internal flow path of the drug delivery device.

In some embodiments, the flexibility of the mount may allow freedom of movement of the cannula that is directionally dependent. For example, the septum contacting portion of the cannula may have a sideways freedom of movement (for example the tip and/or the septum contacting portion of the cannula may move transaxially a distance ranging between 0 to 1.0 mm or under a side load of 0.6 kg). For example, a base may be provided distal to the cannula, blocking backward movement of the cannula (e.g. distal movements of the tip of the cannula and/or movements of the tip of the cannula away from the septum).

In some embodiments the tolerance of deviation of positioning of the access channel of the cartridge with respect to the housing may range for example between 0 to 5 mm and/or between 5 to 7 mm and/or between 7 to 15 the tolerance of orientation of the access channel with the housing may range for example between 0 to 7 degrees. For example, when the cartridge is engaged with the fitting, the tolerance of deviation of positioning of the access channel of the cartridge with respect to the coupling may range for example between 0 to 1 mm in all directions and the tolerance of orientation of the access channel with the coupling may range for example between 0 to 2 degrees.

In performance tests leaks were found to occur during use of patch injectors. Careful observation revealed that leaks were sometimes caused by stresses between a septum puncturing needle and the septum of the cartridge. These stresses may in some instances cause an elastic stretching and/or plastic deformation and/or tearing producing an opening around the piercing location where fluid may leak from the cartridge. A compliant coupling assembly may reduce the stress and/or the leakage.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Connecting a Cartridge to a Fluid Path

Figure 1B:
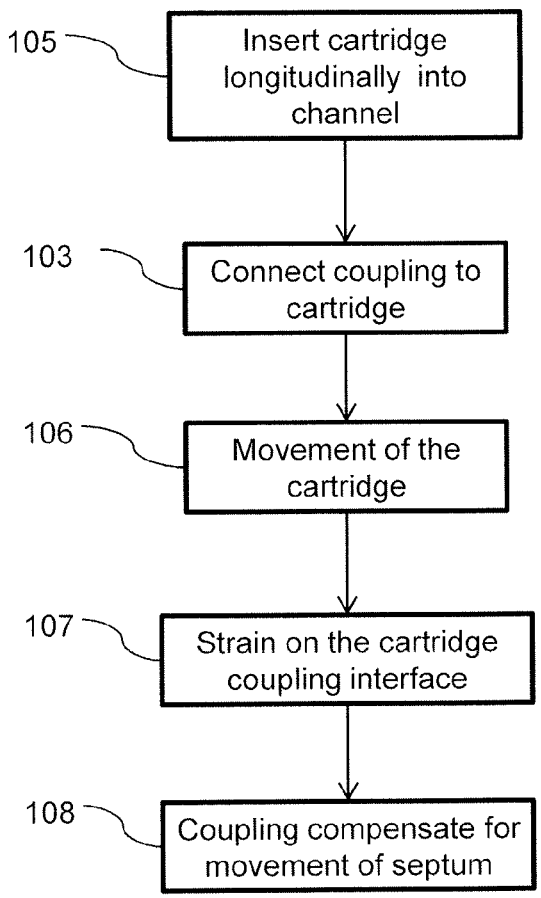

Referring now to the drawings, FIGS. 1A and 1B illustrate methods of connecting a cartridge to a fluid path of a drug delivery device in accordance with some embodiments of the current invention. The drug is optionally supplied in a drug cartridge. In some embodiments, the cartridge may fit to the drug delivery device with a low precision. For example, there may be clearance and/or the cartridge may move while in the drug delivery device. For example, the cartridge may be inserted in a position that is slightly out of alignment with the drug delivery device. Alternatively or additionally, a coupling may move and/or be out of alignment. In some embodiments, the coupling may be mounted in a way that it can move and/or adjust to compensate for misalignments.

In some embodiments a drug cartridge may be contact 101 a cartridge with a misalignment between the cartridge and the coupling. For example, the cartridge may have an access channel sealed by a septum on the distal end thereof and/or the cartridge may be positioned using a guide. In various embodiments, the septum may be slightly misaligned with the cannula of the device. For example misalignment may result from imprecision in positioning of the septum with respect to the body of the cartridge and/or imprecision in positioning of the channel with respect to the housing and/or imprecision in positioning of the channel with respect to the cannula and/or due to unbalanced forces when inserting the cartridge into the channel and/or other factors. Changes in working forces on the cartridge (for example difference between forcing during insertion, waiting, and/or discharge) may cause a cartridge to move after connection of the coupling (e.g. puncturing of a septum). These and/or other factors (for example the bevel of the point of the cannula) may cause the coupling to connect 104 to the cartridge in a misaligned and/or strained state. The coupling and/or a mounting of the coupling may adjust 108 to relieve the strained state. Adjustment 108 of the coupling and/or the coupling mount may allow the coupling to remain in the strained state without stressing the cartridge interface.

In some embodiments a cartridge may be inserted 105 into a delivery device. Optionally, inserting 105 the cartridge into the device may connect 103 a coupling and/or open a path between the drug delivery device and the cartridge. Optionally, the path may be used to supply the drug to the delivery device. For example opening a path between the cartridge and delivery device may include opening a fluid flow path allowing flow of a liquid drug from the cartridge to the delivery device. For example the fluid path may be supplied from the access channel of the cartridge to the coupling of the delivery device.

In some embodiments, parts of the injector may move 106 after the path is opened between the delivery device and the cartridge. For example, a plunger may be pushed into the cartridge to push out the contents. The force of the plunger may cause movement 106 (for example movement of the cartridge and/or the access channel with respect to the housing and/or rotation of the cartridge). For example, the angle between the axis of the cartridge and the guide channel of the delivery device may change. Changes in position of the cartridge may sometime cause transaxial movement of the septum and/or access channel. For example, a cartridge may rotate around its axis. In some cases, a connection between a coupling and the cartridge may be off axis and/or off center. Movement 106 of the cartridge may cause strain 107 on coupling-cartridge interface. Optionally, the coupling may compensate 108, for example by moving along with the cartridge and/or the access channel. An adjustable, flexible, and/or conformable coupling mount optionally preserves the integrity of the flow path and/or preserves the flow path in an open state.

In some embodiments, a septum and/or an axis channel may be moved 106 transaxially a distance that is less than or equal to a movement allowed by a position deviation tolerance of a cartridge guide. Stress on the interface between the septum and the tip region of cannula may develop. The stress may cause compensating movements by the cannula. For example, compensating movements of a magnitude of the position deviation tolerance of the septum may be produced by a stress less than the leak threshold force of the septum. For example, the movement deviation tolerance of the septum in the transaxial direction may range between 0 to 0.5 mm and/or 0.5 to 1.5 mm and/or 1.5 to 3 mm and/or 3 to 6 mm. The threshold leakage force on the septum may for example range between 0.1 to 1 N and/or between 1 N to 5 N and/or between 5 N and/or between 5 to 8 N and/or between 8 to 20 N.

In some embodiments, preserving the flow path may include preserving alignment between the coupling and the access channel. In some embodiments, compensation for the movement of the cartridge may include reducing stress between at an interface between the coupling and the cartridge. In some embodiments, preserving integrity of a flow path and/or reducing stress may reduce and/or prevent leakage of the contents of the cartridge.

States of a Compliant Coupling System

Figure 2:
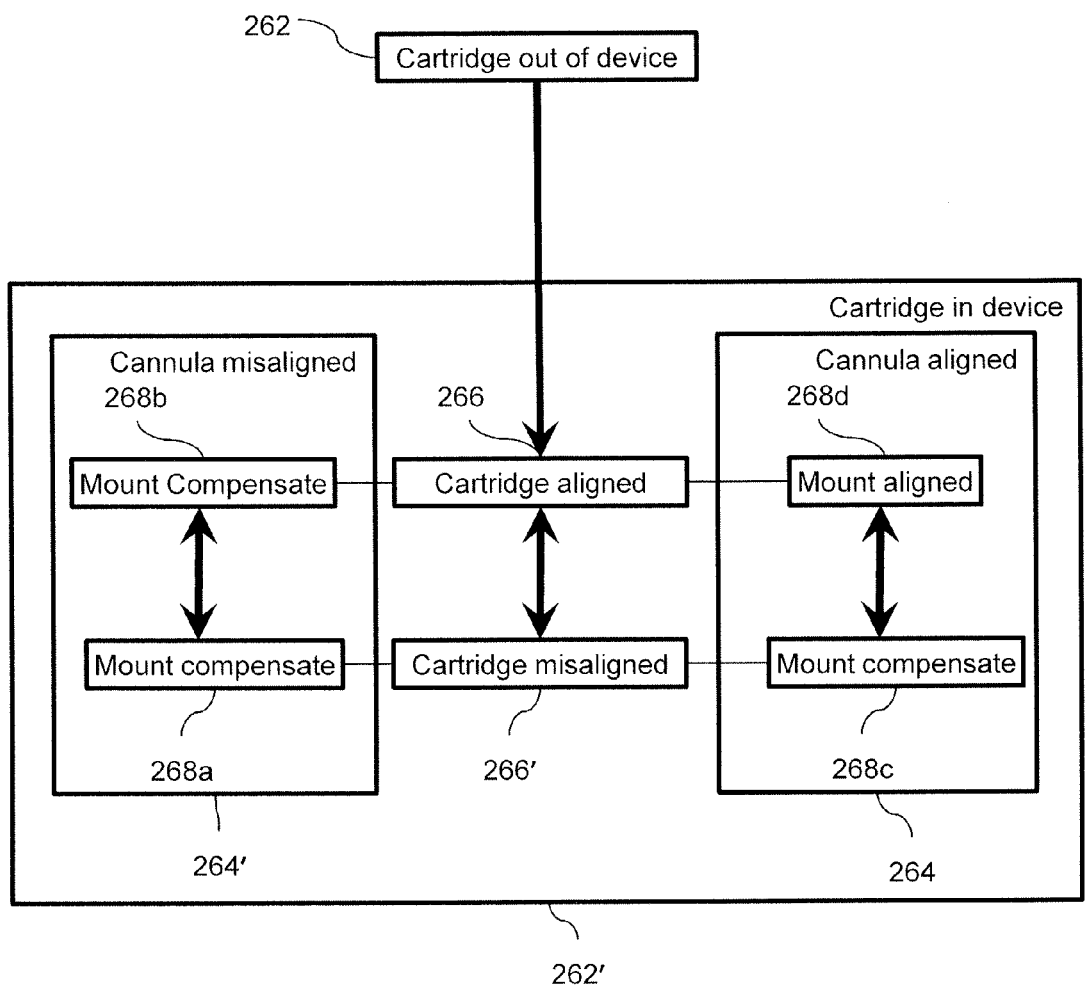
FIG. 2 is a state diagram of a system for connecting a cartridge to a drug delivery device in accordance with an embodiment of the current invention.

FIG. 2 is a state diagram illustrating states of a compliant cartridge coupling assembly in accordance with an embodiment of the current invention. Optionally a coupling assembly may include a compliant mount for a fluid path coupling to an access channel of a cartridge. Optionally, the coupling assembly may compensate for misalignments of one or more parts of the fluid train. For example, the compliant coupling assembly may reduce stress forces on a system under strain. In some embodiments, strain may be caused by misalignment of the cartridge and/or the coupling. For example, the compliant coupling assembly may compensate for misalignment due to machining impressions in the cartridge and/or the housing of the drug delivery device and/or the coupling. Alternatively or additionally, the compliant coupling assembly may compensate for strain caused by changes in alignment due to movement of parts over time.

In some embodiments, a cartridge coupling assembly and/or a cartridge may be connected 262' and/or may be properly aligned 266 without compensation. Connection of the cartridge to a coupling assembly may include for example insertion of the cartridge into a guide in the housing of a drug delivery device. For example, a cartridge may be aligned 266 to a housing of the device and/or a coupling may be aligned 264 to the cartridge and/or the cartridge guide and/or the housing of the device and/or the mount may be aligned 268d with the housing of the device and/or the guide and/or the cartridge.

In some embodiments, compliance (for example flexing and/or pivoting and/or sliding) of the mount of a coupling may compensate 268b for a misalignment 264' of the coupling (for example due to manufacturing imprecision of the coupling and/or the mount and/or the frame).

In some embodiments, flexing of a coupling mount may compensate 268a, for a misalignment 266' and/or movement of a cartridge with respect to a housing of the drug delivery device. Alternatively or additionally, compliance of the mount may compensate 268a, 268c for a misalignment 266' and/or movement of a cartridge with respect to a housing of the drug delivery device.

In some embodiments, a drug cartridge may be supplied disconnected 262 from a drug delivery device. Optionally or alternatively, the cartridge and the device may be integrally manufactured.

A Compliant Coupling Assembly

Figure 3:
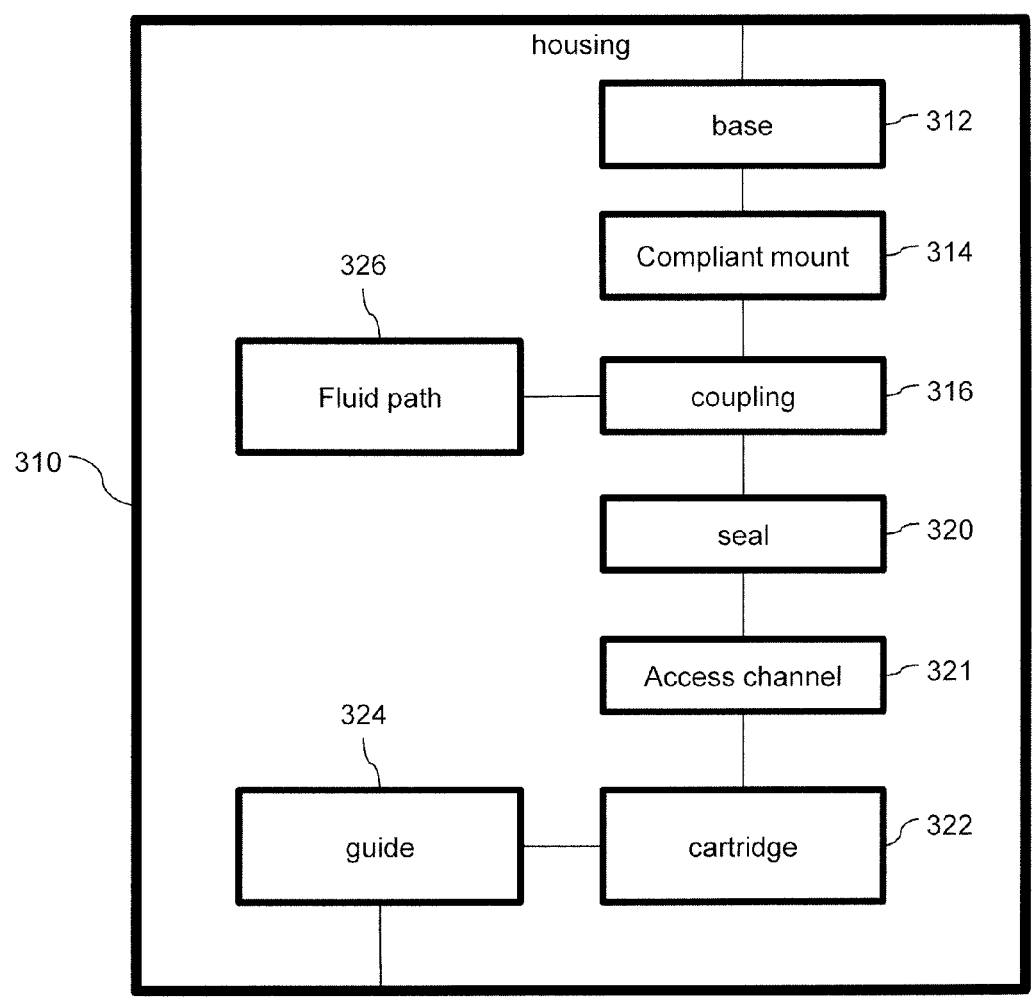
FIG. 3 is a block diagram of a system for connecting a cartridge to a drug delivery device in accordance with an embodiment of the current invention.

FIG. 3 is a block diagram illustrating a compliant coupling assembly in accordance with an embodiment of the current invention. In some embodiments, a housing 310 of a drug delivery device includes a guide 324 for positioning a drug supply cartridge 322 and/or a base 312 supporting a coupling 316. Coupling 316 optionally provides material transport between cartridge 322 and the drug delivery device for example through an internal fluid path 326 of the delivery device. Optionally, coupling 316 may be configured to open a seal 320 (for example seal 320 may include a septum blocking access channel 321). A misalignment between coupling 316 and cartridge 322 and/or movement of cartridge 322 with respect to coupling 316 may cause a disconnection and/or a blockage and/or a leakage. For example, misalignment may be caused by defects in some or all of the parts and/or rough handling of the device. For example the system may include compliant mount 314 supporting coupling 316. Mount 314 may orient coupling 316 with respect to the cartridge. Mount 314 may align and/or position orient coupling 316 with respect to the cartridge 322 and/or an access channel 321 of cartridge 322 and/or guide 324. Mount 314 may be compliant such that coupling 316 may move with respect the cartridge. Optionally fluid path 326 may contain flexible and/or movable components.

In some embodiments, the design of base 312 and/or mount 314 may allow movement of coupling 316 more in one direction than in another. For example, coupling 316 may be allowed to rotate and/or move relatively freely perpendicular to an axis of cartridge 322 and/or guide 324 and/or coupling 316 and/or access channel 321. Movements of coupling 316 toward or away from guide 324 in the direction of a longitudinal axis of axis of cartridge 322 and/or guide 324 and/or coupling 316 and/or access channel 321 may for example be more limited. For example, liming longitudinal movement of coupling 316 may make it easier to connect coupling 316 to access channel 321 and/or cartridge 322, for example when inserting cartridge 322 into the device.

Embodiment for Piercing a Septum of a Cartridge

Figure 4:
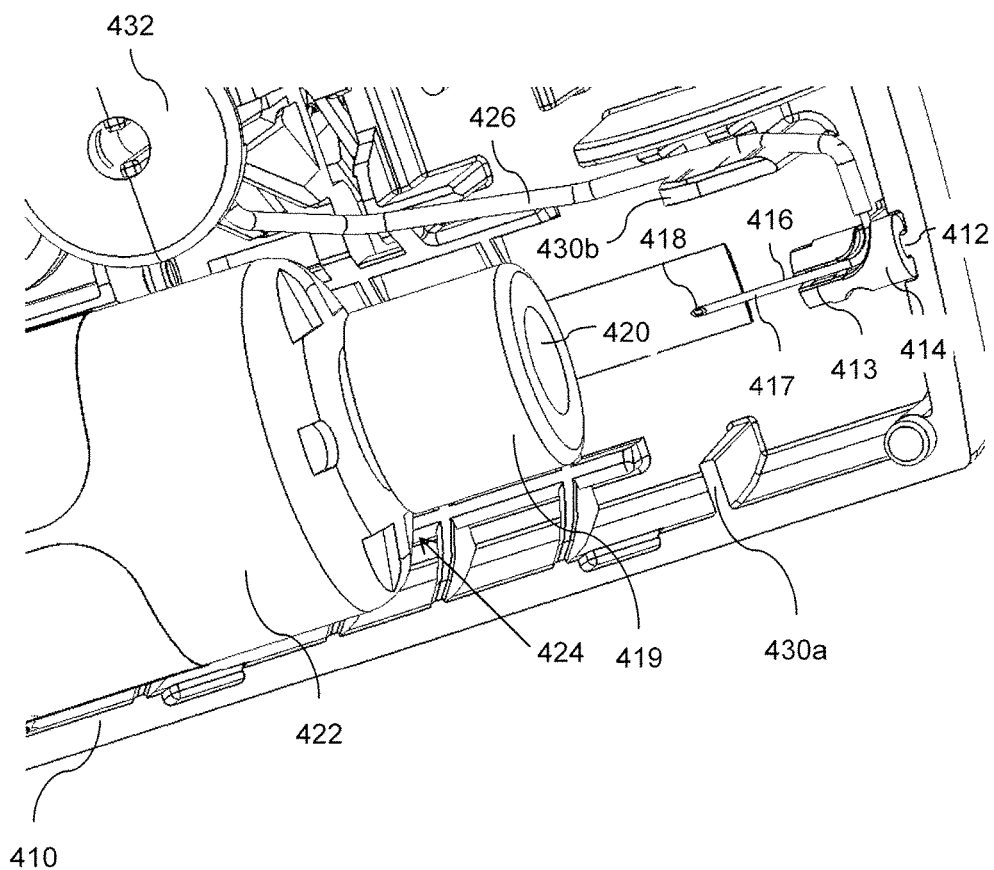
FIG. 4 is perspective illustration of a system for connecting a cartridge to a drug delivery device in accordance with an embodiment of the current invention.

FIG. 4 is a close up dorsal perspective view of a compliant coupling system for a drug delivery device in accordance with an embodiment of the present invention. In the exemplary embodiment of FIG. 4, the coupling system of a drug delivery device includes a cannula 416. In the exemplary embodiment of FIG. 3, the access channel of the cartridge includes an access channel 521 that for example ranges between 1.8 to 2.2 mm wide (see for example FIG. 5B) sealed by a septum 420. Cannula 416 is supported by a mount 414. Optionally mount 414 is flexible. Alternatively or additionally the distal end of mount 414 is supported on housing 410 of the drug delivery device by a pivoting connection to a base 412.

In some embodiment, a coupling may move more freely in one direction than another. For example, base 412 limits longitudinal movement of cannula 416. For example, longitudinal movement of cannula 416 may be limited to a range between 0 and 1 mm. In some embodiments, limiting longitudinal movement cannula 416 may make it easier to insert cannula 416 through septum 420. In some embodiments, pivoting of mount 414 around base may allow transaxial movement (for example lateral movement and/or upward [dorsal] and/or downward [ventral] movement) of the proximal end 418 and/or a septum interface region 417 of coupling 416. For example transaxial movement may range between 0.1 mm and 0.7 mm. For example, when septum 420 moves, stress between the septum and the tip region of cannula 416 may cause compensating movements of the tip region of cannula 416 (for example the tip region may include a tip 418 and/or a septum interface region 417 of cannula 416). For example, a transaxial movement of the septum of 0.7 mm or less may produce a stress on region 417 of the cannula. The stress may produce compensating movement which reduces the stress. For example, compensating movement of region 417 of 0.7 mm may be produced by a stress of less than the leak threshold force of the septum. For example the leak threshold force of the septum may range between 5 to 7 N. Alternatively or additionally the test leak threshold force may be defined under a test pressure for example ranging between 1 to 5 $kg/cm^2$ and/or between 5 to 6 $kg/cm^2$ and/or between 6 to 12 $kg/cm^2$. Alternatively the leak volume may range for between 0.01 to 0.05 ml and/or between 0.05 to 0.1 ml and/or between 0.1 to 0.2 ml and/or between 0.2 to 0.5 ml and/or between 0.5 to 1 ml. The leak volume may be defined over a given time (for example the volume may leak out over a time ranging between 0 and 60 seconds and/or between 1 to 10 minutes and/or between 10 minutes to an hour and/or between an hour to a day). A leak threshold strain may be defined for example as a quantity of movement of a cannula puncturing a septum that causes leaking between the cannula and the septum, for example leakage of more than 0.05 ml under working conditions. Alternatively or additionally the test leak threshold strain may be defined under a test pressure for example ranging between 1 to 5 $kg/cm^2$ and/or between 5 to 6 $kg/cm^2$ and/or between 6 to 12 $kg/cm^2$. Alternatively the leak volume may range for between 0.01 to 0.05 ml and/or between 0.05 to 0.1 ml and/or between 0.1 to 0.2 ml and/or between 0.2 to 0.5 ml and/or between 0.5 to 1 ml.

In some embodiments, mount 414 may be configured to allow more movement under some conditions than others. For example, mount 416 is configured to inhibit more transaxial movement when there is a longitudinal force in the proximal direction on mount 414. For example, when there is no distal force, mount 414 sits on base 412 and may pivot relatively freely. A distal force (for example the force of septum 420 being pushed against cannula 416 optionally pushes the rear (distal) portion of mount 414 against the rear (distal) wall of housing 410. When braced against the rear wall of housing 410, mount 414 is more stable. In some embodiments, added stability under a distal force may make it easier to puncture septum 420 with cannula 416. Alternatively or additionally, base 412 may be located off the center axis of mount 414. For example, base 412 may be offset slightly (rightward on the page of FIG. 5A) away from the bending direction of cannula 416 to offset the natural tendency of cannula 416 to twist away from its bent leg under distal forces. For example, base 412 may be offset slight in the ventral direction (into the page of FIG. 5A) such that under distal forces, base 412 offsets the tendency of cannula 416 to twist ventrally opposite the dorsal orientation of the face of the bevel of tip 418. Optionally when there is no distal force the slight axial offset of the positioning of base 412 may have a negligible biasing effect on movement of cannula 416. Alternatively or additionally, a channel 413 may be configured to bias the movements of cannula 416. For example, channel 413 in which cannula 416 is supported is open in the dorsal direction. Optionally the open dorsal face of channel 413 allows more freedom of movement to cannula 416 in the dorsal direction.

In some embodiments, cannula 416 may include a hollow bore needle ranging between 10 to 34 gauge. Mount 414 may be made for example of a hard plastic or resin for example Polycarbonate. Alternatively mount 414 may be made of a more flexible material for example an elastomer, for example thermoplastic elastomer (TPC) and/or rubber and/or silicone. In some embodiments the mount may be connected to a frame (e.g. housing 410) on a movable support for example a pivot and/or a sliding support. Movement of the movable support optionally supplies the compliance of the mount. In some embodiments, the length of the axis channel (for example the neck of the cartridge) may range between 6 and 10 mm. For example the diameter of the axis channel (for example the neck of the cartridge) may range between 4 to 8 mm and/or between 8 to 8.5 mm and/or between 8.5 to 9 mm and/or between 9 to 10 mm and/or between 10 to 20 mm.

In some embodiments, an internal fluid path connecting the coupling to a delivery subassembly may include a flexible section. For example, an internal fluid path of the embodiment of FIG. 4 connects a coupling to a patient interface, for example a needle insertion assembly 432. The fluid path optionally includes a flexible tube 426. In some embodiments, the flexibility of tube 426 allows the couple to move without large resistance from and/or breakage of fluid path. Optionally the tube may be made for example of Silicone or Tygon. The length of the tube may range for example between 10 to 100 mm. The inner diameter of the tube may range for example between 0.1 to 3 mm.

In some embodiments, a cartridge may be steadied by supports. For example, when cartridge 422 is inserted fully into guide channel 424 (into a loaded position) supports 430a and 430b may steady an adapter fitting 419 of cartridge 422. Steadying the position of adapter fitting 419 may increase the precision of positioning and/or decrease movement of channel 521.

Figure 5:
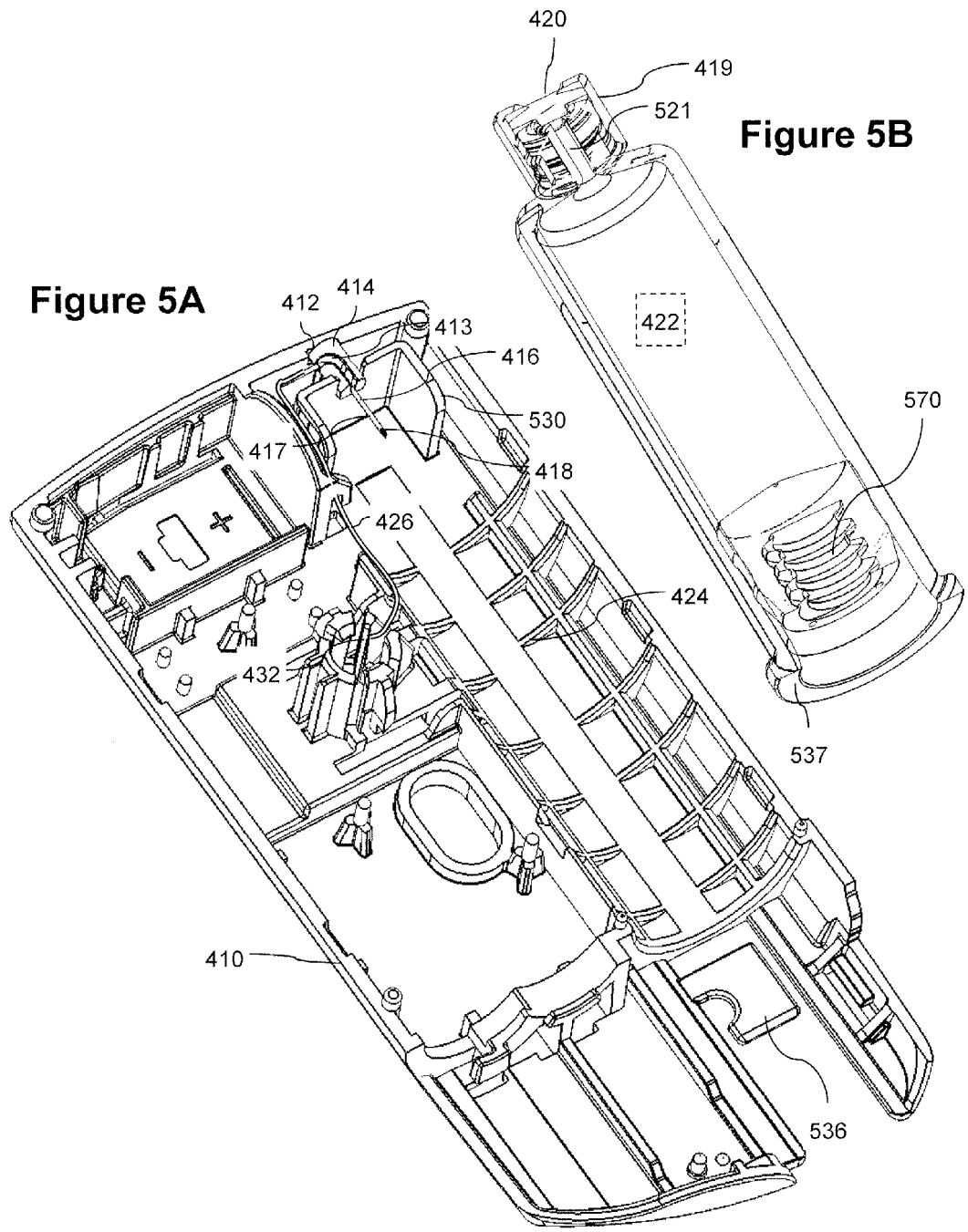
FIG. 5A is perspective illustration of a system for connecting a cartridge installed into a lower housing a drug delivery device in accordance with an embodiment of the current invention.
FIG. 5B is cross section illustration of a cartridge in accordance with an embodiment of the current invention.

FIG. 5A is a dorsal perspective view of a compliant coupling assembly inside an open drug delivery device in accordance with an embodiment of the present invention. In FIG. 5A, the proximal side of mount 414 can be seen protruding through a hole in a cartridge support 530. The proximal portion of cannula 416 is seen extending proximally from mount 414. Optionally the proximal end of cannula 416 includes a sharpened tip 418. In some embodiments, mount 414 is flexible. Flexibility of mount 414 optionally adds a degree of freedom to the system. For example, flexibility of mount 414 may reduce forces on the interface between the delivery device and the cartridge (for example septum 420) caused by bending of cannula 416 and/or misalignment of mount 414 and housing 410 and/or misalignment of septum 420 and fitting 419.

In some embodiments, supports may align a cartridge in a drug delivery device. Optionally support 530 which aligns cartridge 422 also holds compliant mount 414. Optionally, a slack (for example a space between support 530 fitting 419) allows a limited freedom of movement of cartridge 422 with respect to housing 410, for example ranging between 0.01 mm and 1.0 mm. Optionally mount 414 may give a freedom of movement to a proximal portion of cannula 416. For example the freedom of movement may be in the horizontal direction and/or the vertical direction and/or there may be a greater freedom of movement in one direct than the other. For example, the freedom of movement may be to the portion of cannula 416 extending proximally to mount 414 and/or to septum interface portion 417 of the needle and/or the proximal tip 418 of the needle. The freedom of movement may range between 30 to 60% of the freedom of movement of cartridge 422 and/or between 60 to 120% and/or between 120% and 200% to the freedom of movement of cartridge 422 and/or channel 521.

In some embodiments, cannula 416 may include a bent needle, a proximal side of which couples to cartridge 422 (for example by piercing septum 420) and a distal side of which is connected to an internal fluid path (for example flexible tube 426) and/or to an output assembly such as needle insertion assembly 432. Mount 414 optionally includes a curved channel 413 through which fits the bent portion of cannula 416. Optionally, cannula 416 may be bent between 30 to 80 degrees.

In some embodiments, cartridge 422 is inserted into a distal opening in guide channel 424. Optionally, cartridge 422 slides longitudinally along channel 424 until it reaches a loaded position. For example in the loaded position, the coupling (e.g. cannula 426) engages the access channel of cartridge 422, for example by puncturing septum 420 and/or sliding into channel 521 (e.g. see FIG. 5B). An optional locking latch 536 locks cartridge 422 into guide channel 424. For example latch 536 blocks outward movement of a flange 537 on the proximal end of cartridge 422.

FIG. 5B is a cross sectional view of a drug cartridge for a drug delivery device in accordance with an embodiment of the present invention. The cross section view of cartridge 422 illustrates for example a narrowed access channel 521 of cartridge 422. An exemplary plunger 570 is illustrated near the proximal end of cartridge 422. Cartridge 422 optionally includes a distal flange 537.

Figure 6:
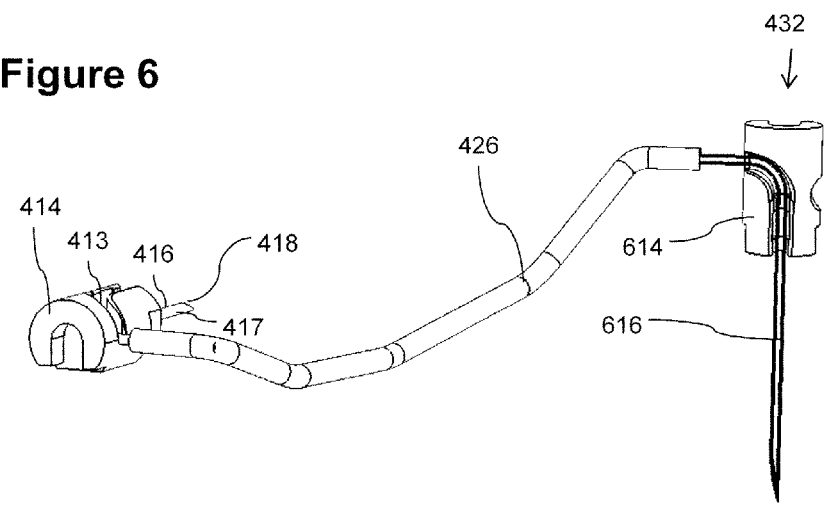
FIG. 6 is perspective illustration of fluid path of a system for connecting a cartridge and a drug delivery device in accordance with an embodiment of the current invention.

FIG. 6 is a distal view of a compliant coupling assembly in accordance with an embodiment of the current invention. FIG. 6 further illustrates details of needle insertion assembly 432 which optionally includes a bent needle 616 (for example a hypodermic needle for insertion into a patient) connected to tube 426 and/or a mount 614 with a curved channel.

Figure 7:
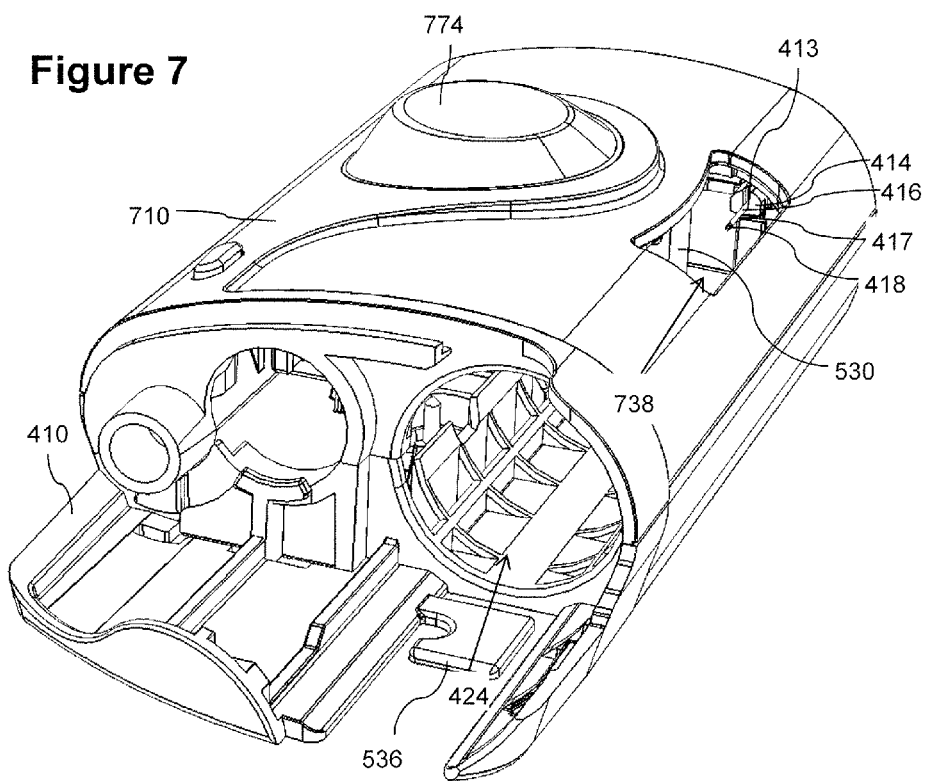
FIG. 7 is perspective illustration of the outside of a drug delivery device in accordance with an embodiment of the current invention.

FIG. 7 is a proximal/dorsal perspective view of the exterior of a delivery device including compliant coupling assembly in accordance with an embodiment of the present invention. The compliant coupling assembly is seen through a window 738 in an upper housing section 710 of the injector. An optionally activation button 774 is shown.

Figure 8:
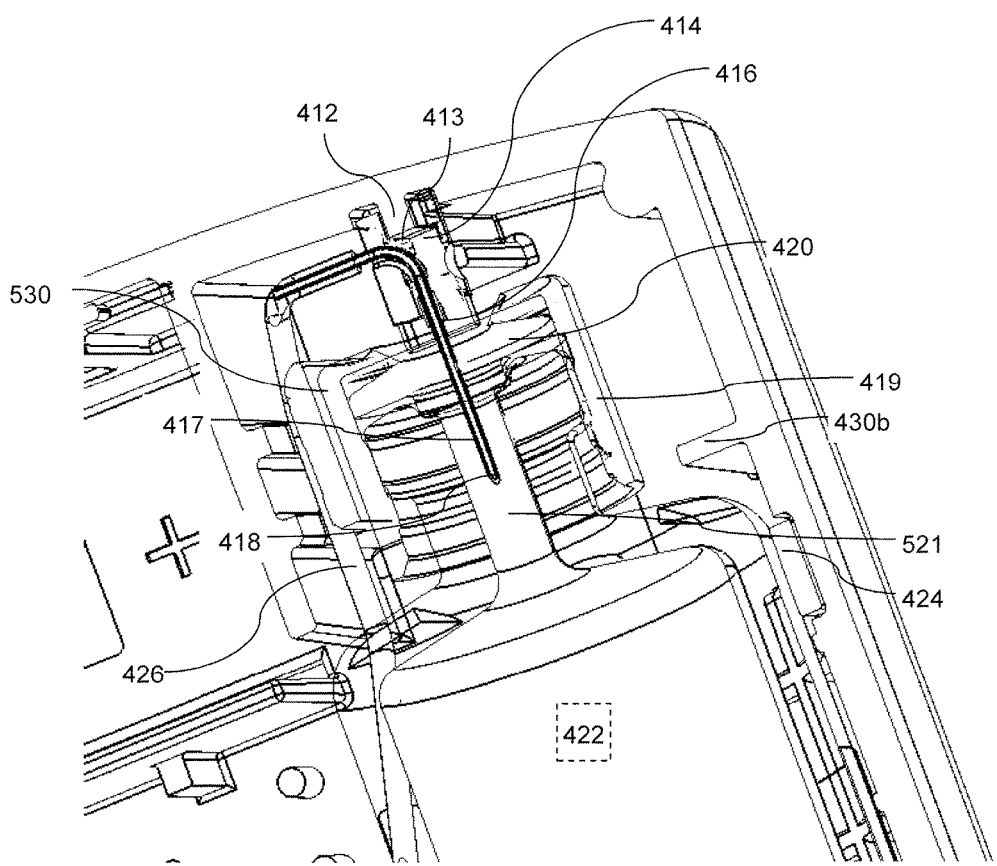
FIG. 8 is cross sectional illustration of a system for connecting a cartridge to a drug delivery device in accordance with an embodiment of the current invention.

FIG. 8 is a distal cross sectional view (cut along a horizontal plane passing through the middle of cartridge 422 and/or cannula 416) of a compliant coupling assembly of a drug cartridge in a loaded position in accordance with an embodiment of the present invention. Optionally, the in loaded position, cannula 416 has been inserted through septum 420 into channel 521. Optionally cannula 416 forms a fluid path from the inside of cartridge 422 to tube 426.

Figure 9:
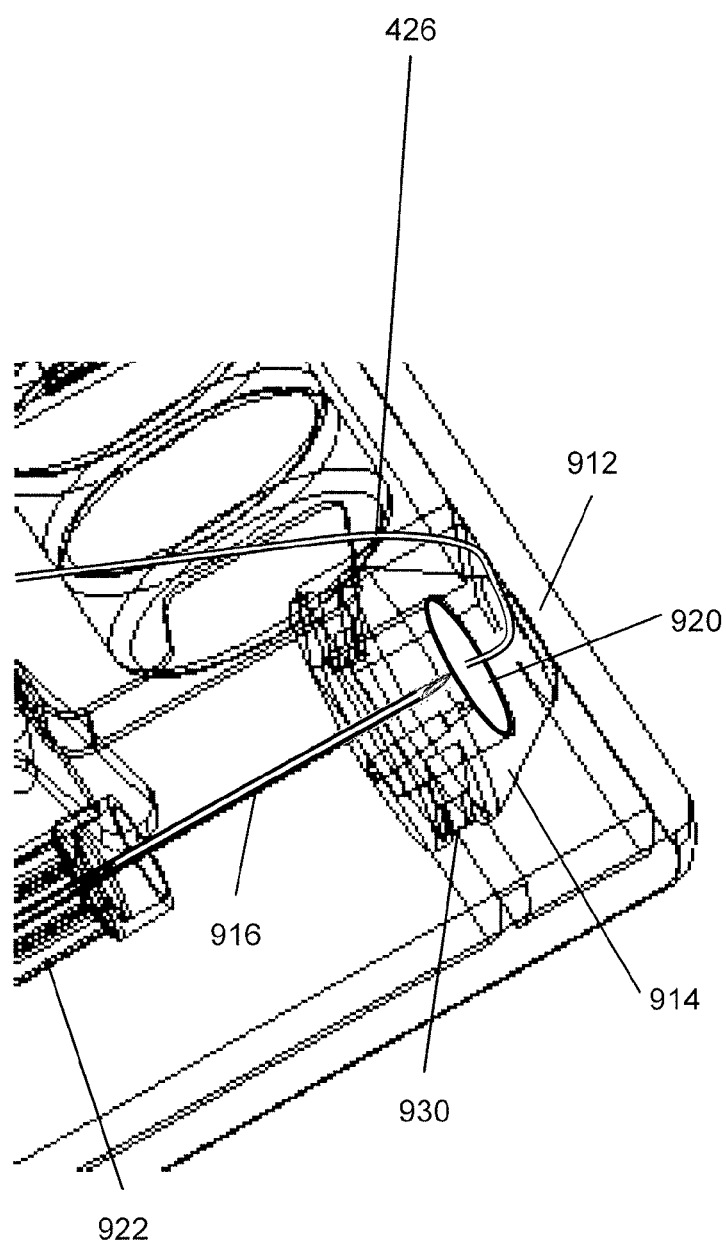
FIG. 9 is perspective illustration of a system for connecting a cartridge to a drug delivery device in accordance with an embodiment of the current invention.

FIG. 9 is a proximal perspective view compliant coupling assembly to an access channel of a drug cartridge installed in a delivery device in accordance with an embodiment of the present invention. For example, in the embodiment of FIG. 9, the coupling of the compliant coupling assembly includes a septum 920. Optionally in the exemplary embodiment of FIG. 9 the cartridge includes a cannula for piercing septum 920. In some embodiment, septum 920 may be mounted on a compliant mount 914. Optionally, compliant mount 914 allows a defined freedom of transaxial movement to septum 920. For example, the compliance of mount 914 may compensate for transaxial movements and/or rotation of cartridge 922 and/or needle 916. For example, mount 914 may compensating for transaxial movement of needle 916 without stressing the interface between the needle 916 beyond a leak threshold stress on septum 920. A support 930 connected for example to a slit in the side of mount 914 and/or a base 912 distal to mount 914 may limit longitudinal movements of septum 920. For example, limiting longitudinal movements may make it easier to pierce septum 920 with cannula 916.

Figure 10A:
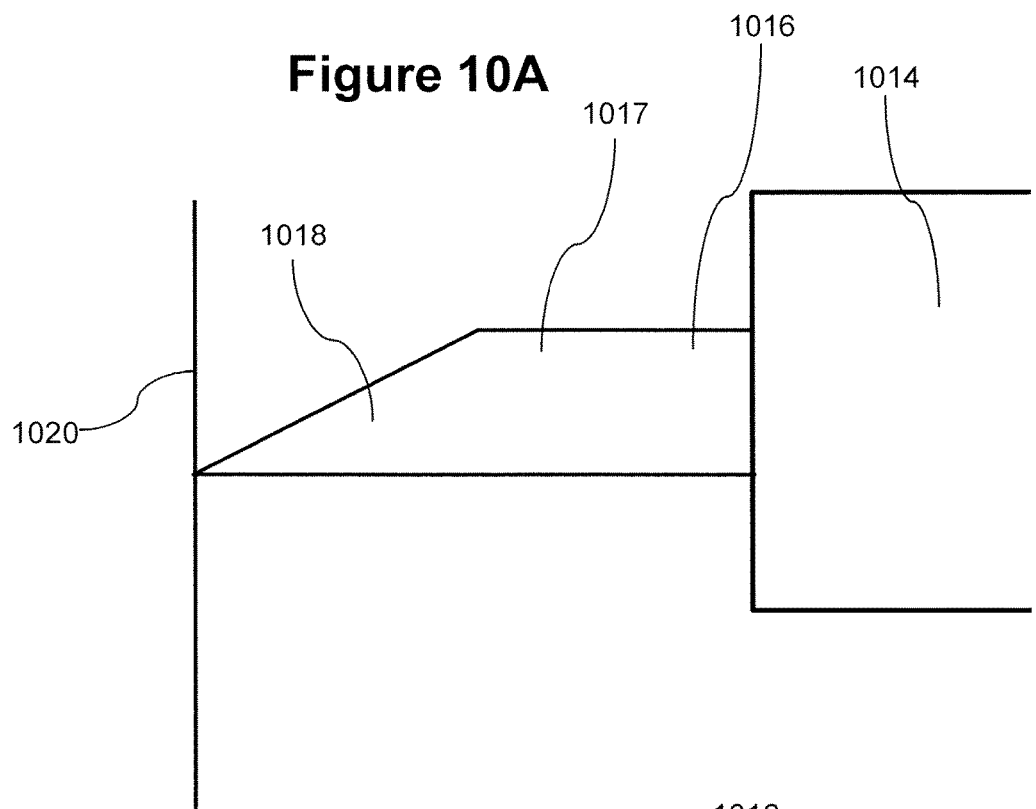
Figure 10B:
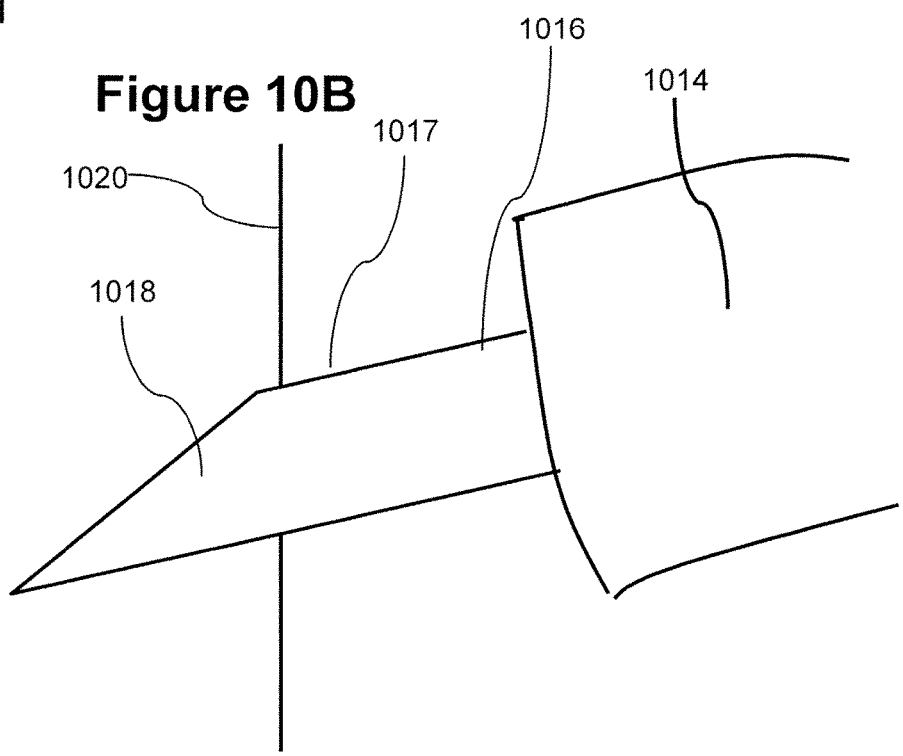

FIGS. 10A-10C illustrate a proximal close up perspective view of a compliant coupling assembly in accordance with an embodiment of the current invention. In some embodiments, a compliant mount 1014 holds a coupler including a cannula 1016. Optionally, when cannula 1016 pierces septum 1020, the beveled tip 1018 may be translated transaxially. For example in FIG. 10B cannula 1016 is oriented with the bevel of tip 1018 facing upward (dorsally). In some cases, when tip 1018 penetrates septum 1020 it for a hole off center. For example, for a beveled tip, a hole is formed at the point of the needle which may be located off the axis of the needle by half the width of the cannula. Alternatively or additionally, when the cannula is directed at an angle to the direction of movement between the septum and the cannula, a hole may be produced off the axis. In the example of FIGS. 10A-10C, the beveled tip 1018 of cannula 1016 is located off center (e.g. below and/or ventral) to the axis of cannula 1016 by half the width (e.g. diameter) of cannula 1016. As cannula 1016 is inserted through the off axis hole, cannula 1016 is deflected downward (e.g. ventrally) for example as illustrated in FIGS. 10B and 10C.

In some embodiments, a cannula may be inserted through a septum until a septum interface region intersects the septum. For example, FIG. 10C illustrates cannula 1016 positioned with septum interface region 1017 intersecting septum 1020. For example, septum interface region 1017 may be located 3.5 mm from tip 1018 of cannula 1016 and/or 2.5 mm from the proximal point of connection between cannula 1016 and mount 1014. For example a rigid mount and steel cannula may produce a force due to the deflection and/or bending of the cannula that is greater than the leak threshold of septum 1020. For example, a septum leak threshold force of the septum may range between 6 to 7 N. In some cases forces greater than the leak threshold may result in tearing of the septum in the direction of the bevel and/or leaking of the septum from behind the bevel. Optionally, compliant mount 1014 may allow deflection of septum interface region with less stress than the bending stress of the cannula and/or a septum leak threshold. For example, compensating movement and/or flexing of mount 1014 may avoid producing a tear and/or leak in septum 1020.

In some embodiments, a cartridge may rotate around its longitudinal axis. For example this may cause septum 1020 to rotate. In some cases, for the example of FIGS. 10A-10C where cannula has punctured septum 1020 off center) such rotation may cause twisting of cannula 1016. Compliant mount 1014 may be configured to allow such twisting without producing a force greater than a leakage threshold between septum interface region 1017 of cannula 1016 and septum 1020.

It is expected that during the life of a patent maturing from this application many relevant technologies will be developed and the scope of the terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An assembly for coupling a drug delivery device to a cartridge sealed by a septum, the assembly comprising:
   an axially extending cannula having a tip region configured to penetrate the septum, said tip region having a width; and
   a frame including:
   an axially extending guide sized and shaped to secure the cartridge to said frame; and
   a mount pivotably positioned on said frame, the cannula being attached to said mount such that said tip region of said cannula protrudes through the septum of the cartridge when said cartridge is secured to said frame by said guide;
   wherein a requisite degree of movement between the cannula and the septum at an interface therebetween to cause leakage at the interface defines a leak threshold force of the septum, and
   wherein said mount permits transaxial movement of said tip region of said cannula by at least a distance equal to the width of the tip region in response to a force applied to the cannula at the interface between the cannula and the septum of less than the leak threshold force.

2. The assembly of claim 1, wherein a force of less than a leak threshold force of said septum moves said tip region of said cannula transaxially at least a distance equal to a position deviation tolerance of said septum.

3. The assembly of claim 1, wherein said distance is greater than a movement caused by a flexibility of said frame and said cannula under said leak threshold force.

4. The assembly of claim 1, wherein said mount compensates for a movement of said cannula at a stress level less than a bending stress of said cannula.

5. The assembly of claim 1, wherein said leak threshold force is 6 N.

6. The assembly of claim 1, further comprising:
   a base located on a side of said cannula opposite said tip region, said base inhibiting backwards movement of said tip region.

7. The assembly of claim 6, wherein said base is positioned off axis of said cannula.

8. The assembly of claim 1, wherein said mount is configured to bias movement of said cannula in a particular direction.

9. The assembly of claim 8, wherein said particular direction is parallel to a face of a bevel of a tip of said cannula.

10. The assembly of claim 1, wherein said cannula is bent at an angle ranging between 30 to 80 degrees.

11. The assembly of claim 1, wherein a second end of said cannula is connected to a flexible fluid path.

12. The assembly of claim 1, wherein the cartridge is coupleable to said cannula by a linear movement of the cartridge with respect to the guide.

13. The assembly of claim 1, wherein said compliant mount is flexible.

\* \* \* \* \*